US010260965B2

(12) United States Patent
Ikeda et al.

(10) Patent No.: US 10,260,965 B2
(45) Date of Patent: Apr. 16, 2019

(54) HEAT FLOW METER AND ELECTRONIC DEVICE

(71) Applicant: SEIKO EPSON CORPORATION, Tokyo (JP)

(72) Inventors: Akira Ikeda, Chino (JP); Sakiko Shimizu, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 308 days.

(21) Appl. No.: 15/053,531

(22) Filed: Feb. 25, 2016

(65) Prior Publication Data

US 2016/0252407 A1    Sep. 1, 2016

(30) Foreign Application Priority Data

Feb. 27, 2015  (JP) ................................. 2015-037885

(51) Int. Cl.
| | |
|---|---|
| *G01K 17/00* | (2006.01) |
| *A61B 5/01* | (2006.01) |
| *G01K 13/00* | (2006.01) |
| *A61B 5/00* | (2006.01) |

(52) U.S. Cl.
CPC .............. *G01K 13/002* (2013.01); *A61B 5/01* (2013.01); *A61B 5/681* (2013.01); *G01K 17/00* (2013.01); *A61B 2562/0271* (2013.01); *A61B 2562/04* (2013.01)

(58) Field of Classification Search
None
See application file for complete search history.

(56) References Cited

U.S. PATENT DOCUMENTS

| | | | |
|---|---|---|---|
| 4,541,728 A * | 9/1985 | Hauser | G01N 25/18 374/29 |
| 5,524,618 A | 6/1996 | Pottgen et al. | |
| 5,813,994 A | 9/1998 | Pottgen et al. | |
| 6,238,354 B1 * | 5/2001 | Alvarez | G01K 1/024 374/100 |
| 7,020,508 B2 | 3/2006 | Stivoric et al. | |

(Continued)

FOREIGN PATENT DOCUMENTS

| | | |
|---|---|---|
| JP | S57-183832 A | 11/1982 |
| JP | S61-135239 U | 8/1986 |

(Continued)

OTHER PUBLICATIONS

Jul. 12, 2016 Extended Search Report issued in European Patent Application No. 16157600.4.

*Primary Examiner* — Clayton E. LaBalle
*Assistant Examiner* — Leon W Rhodes, Jr.
(74) *Attorney, Agent, or Firm* — Oliff PLC

(57) ABSTRACT

A heat flow sensor includes a heat transfer layer that has first and second surfaces confronting each other and has flexibility and a temperature difference measurement unit that measures a temperature difference between the first and second surfaces of the heat transfer layer. The heat transfer layer includes a first member having flexibility and a second member with higher thermal conductivity than the first member. The thickness of the heat transfer layer is equal to or greater than 0.5 mm, thermal conductivity of the heat transfer layer is equal to or greater than 10 W/(m×K), and Shore hardness of the heat transfer layer is equal to or less than A50.

10 Claims, 9 Drawing Sheets

(56) References Cited

U.S. PATENT DOCUMENTS

| | | | |
|---|---|---|---|
| 7,699,520 B2 * | 4/2010 | Yoo | G01K 17/20 374/29 |
| 7,765,811 B2 * | 8/2010 | Hershberger | H01L 35/30 136/203 |
| 7,942,825 B2 * | 5/2011 | Ranganathan | A61B 5/01 374/107 |
| 8,663,106 B2 | 3/2014 | Stivoric et al. | |
| 8,979,763 B2 | 3/2015 | Stivoric et al. | |
| 2007/0181650 A1 | 8/2007 | Yoo et al. | |
| 2007/0206655 A1 * | 9/2007 | Haslett | A61B 5/01 374/141 |
| 2010/0158069 A1 | 6/2010 | Yoo et al. | |
| 2010/0198322 A1 * | 8/2010 | Joseph | A61F 7/007 607/108 |
| 2011/0069459 A1 | 3/2011 | Padiy | |
| 2012/0024833 A1 | 2/2012 | Klewer et al. | |
| 2013/0087180 A1 * | 4/2013 | Stark | H01L 35/30 136/205 |
| 2016/0066839 A1 | 3/2016 | Ikeda et al. | |
| 2016/0163949 A1 * | 6/2016 | Stark | H01L 35/08 136/212 |

FOREIGN PATENT DOCUMENTS

| | | |
|---|---|---|
| JP | S61-165436 U | 10/1986 |
| JP | 2004-267788 A | 9/2004 |
| JP | 2007-208262 A | 8/2007 |
| JP | 2011-120917 A | 6/2011 |
| JP | 2016-057198 A | 4/2016 |
| JP | 2016-133484 A | 7/2016 |

* cited by examiner

HEAT FLOW METER AND ELECTRONIC DEVICE

CROSS REFERENCE

This application claims the benefit of Japanese Patent Application No. 2015-37885, filed on Feb. 27, 2015. The content of the aforementioned application is incorporated herein by reference in its entirety.

BACKGROUND

1. Technical Field

The present invention relates to a heat flow meter and an electronic device.

2. Related Art

A human body temperature is maintained by heat emitted from a human body. Metabolism for maintaining this body temperature is called basal metabolism. Accordingly, when the heat emitted from a human body is measured, a metabolic rate can be known. As paths of heat emitted from a human body, there are convective heat transfer in which heat is transferred to an external environment by convection of air, water, or the like and radiative heat transfer in which heat is transferred to the surface of a surrounding object by radiation of electromagnetic waves. When a heat flow by heat transfer such as the convective heat transfer or the radiative heat transfer is measured, heat (a heat discharge) emitted from a human body can be measured.

For example, JP-A-2011-120917 discloses a technology for mounting an armband-shaped electronic device (sensor device) including a heat flow sensor (heat flux sensor) to come into contact with a skin of a wearer and measuring a heat flow from a temperature difference occurring inside the heat flow sensor by the heat transfer.

Incidentally, to accurately measure a heat flow emitted from a human body, it is necessary to transfer heat of a skin surface to the heat flow sensor without loss. The electronic device disclosed in JP-A-2011-120917 has a structure in which an attachment having flexibility and formed of metal or the like having good thermal conductivity is brought into contact with a skin surface so that heat of the skin surface is transferred to the heat flow sensor via the attachment since the heat flow sensor has no flexibility. In such a structure, however, part of the heat from the skin surface may flow out to another member before the heat is transferred to the heat flow sensor, and thus an error may occur in measurement of the heat flow.

When the heat flow sensor with no flexibility is brought into direct contact with an object having a curved surface such as a human body to suppress the transfer loss caused due to outflow of the heat, an air layer easily occurs between the heat flow sensor and the skin surface. When the air layer occurs between the heat flow sensor and the skin surface, an actual contact area between the heat flow sensor and the skin surface decreases, and thus the heat transferred to the heat flow sensor decrease. Therefore, the measured heat flow is less than the actual heat flow. As a result, a problem arises in that an error of measurement of the heat flow occurs in the heat flow sensor with no flexibility, and thus measurement accuracy of a heat discharge frost a human body deteriorates.

SUMMARY

An advantage of some aspects of the invention is to solve at least a part of the problems described above, and the invention can be implemented as the following forms or application examples.

APPLICATION EXAMPLE 1

A heat flow meter according to this application example includes: a heat transfer unit that has first and second surfaces confronting each other and has flexibility; and a temperature difference measurement unit that measures a temperature difference between the first and second surfaces of the heat transfer unit.

According to the configuration of this application example, in the heat flow meter, the temperature difference measurement unit can measure the temperature difference between the first and second surfaces of the heat transfer unit having the flexibility and measure a beat flow by heat transfer. For example, when the first surface of the heat transfer unit is brought into contact with a human body (arm) or the like and a heat flow is measured, the heat transfer unit has the flexibility, and thus is fitted to the surface (skin surface) of the arm. Therefore, since close contact with the skin surface is improved and an air layer rarely occurs between the heat transfer unit and the skin surface, a decrease in a contact area is suppressed. As a result, since an error can decrease in measurement of the heat flow generated between the skin surface coming into contact with the first surface and the external environment coming into contact with the second surface, the heat discharge of the human body can be measured with high, accuracy.

APPLICATION EXAMPLE 2

In the heat flow meter according to the application example, it is preferable that the heat transfer unit includes a first member having flexibility and a second member with higher thermal conductivity than the first member.

In the configuration of this application example, the heat transfer unit includes the first member having the flexibility and the second member with the higher thermal conductivity than the first member. Therefore, the heat transfer unit is configured using the first member having the flexibility as a base member and thermal conductivity can be assigned to the second member.

APPLICATION EXAMPLE 3

In the heat flow meter according to the application example, it is preferable that a thickness of the heat transfer unit is equal to or greater than 0.5 mm, thermal conductivity of the heat transfer unit is equal to or greater than 10 W/(m×K), and Shore hardness of the heat transfer unit is preferably equal to or less than A50.

In the configuration of this application example, the thickness of the heat transfer unit is equal to or greater than 0.5 mm, a temperature difference for measuring a heat flow can be generated in a thickness direction between the first and second surfaces. Since the thermal conductivity of the heat transfer unit is 10 W/(m×K) and is greater than conductivity of general rubber, this material can be suitable for the material of the heat transfer unit. Since the Shore hardness of the heat transfer unit is equal to or less than A50, it is possible to improve the flexibility of the heat transfer unit.

APPLICATION EXAMPLE 4

In the heat flow meter according to the application example, it is preferable that a heat diffusion layer with thermal conductivity greater than 100 W/(m×K) is disposed on the first surface.

In the configuration of this application example, since the heat diffusion layer with the larger thermal conductivity than the heat transfer unit is disposed on the first surface of the heat transfer unit, temperature distribution on the plane of the first surface can be caused to be further uniform. Therefore, the heat flow can be measured in a more stable state even when a variation occurs due to a contact state with the skin surface or a variation occurs due to the temperature distribution of the skin surface at the time of the measurement of the heat flow.

APPLICATION EXAMPLE 5

In the heat flow meter according to the application example, it is preferable that Shore hardness of the heat diffusion layer is equal to or less than A50.

In the configuration of this application example, since the Shore hardness of the heat diffusion layer disposed on the first surface is equal to that of the heat transfer unit, the flexibility of the heat transfer unit is not damaged.

APPLICATION EXAMPLE 6

In the heat flow meter according to the application example, it is preferable that a protective layer formed of an organic substance is disposed on a surface of the heat diffusion layer.

In the configuration of this application example, since the protective layer is disposed on the surface of the heat diffusion layer, the heat diffusion Layer and the heat transfer unit can be protected against contact with an external object.

APPLICATION EXAMPLE 7

In the heat flow meter according to the application example, it is preferable that the Shore hardness of the protective layer is equal to or less than A50.

In the configuration of this application example, since the Shore hardness of the protective layer disposed on the surface of the heat diffusion layer is equal to that of the heat diffusion layer and the heat transfer unit, the flexibility of the heat transfer unit and the heat diffusion layer is not damaged.

APPLICATION EXAMPLE 8

In the heat flow meter according to the application example, it is preferable that the heat transfer unit, the heat, diffusion layer, and the protective layer are joined to each other by sewing.

In the configuration of this application example, since the heat transfer unit, the heat diffusion layer, and the protective layer are joined to each other by the sewing. The mutual joining strength can be improved without damage to the flexibility of the entire heat flow meter.

APPLICATION EXAMPLE 9

In the heat flow meter according to the application example, it is preferable that the temperature difference measurement unit measures a temperature difference based on temperature information at a plurality of points of the first surface and temperature information at a plurality of points of the second surface.

In the configuration of this application example, since the temperature difference is measured based on temperature information at a plurality of points on each of the first and second surfaces, the temperature distribution in the plane of the first surface can be averaged. Therefore, the heat flow generated between the skin surface and the external environment can be measured in a more stable state even when a variation occurs due to a contact state between the surface of the arm and the first surface, a variation occurs due to the temperature distribution of the surface of the arm, or a variation occurs due to the temperature distribution in the external environment with which the second surface comes into contact at the time of the measurement of the heat flow.

APPLICATION EXAMPLE 10

An electronic device according to this application example includes; a belt on which a heat flow meter including a heat transfer unit that has first and second surfaces confronting each other and has flexibility and a temperature difference measurement unit that measures a temperature difference between the first and second surfaces of the heat transfer unit is mounted; a casing that is connected to the belt; and a control unit that is provided inside the casing. The control unit controls the heat flow meter.

In the configuration of this application example, the electronic device includes the belt on which the foregoing heat flow meter is counted and the casing in which the control unit controlling the heat flow meter is provided. Therefore, for example, when the electronic device is mounted on a human body (arm) using the belt and a heat discharge from a human body is measured, an air layer rarely occurs between the heat flow meter and the skin surface. Therefore, since an error can decrease in the measurement of the heat flow generated between the skin surface and the external environment, the electronic device measuring the heat discharge from the human body with high accuracy can be provided.

APPLICATION EXAMPLE 11

In the electronic device according to the application example, it is preferable that thermal conductivity of the belt is less than thermal conductivity of the heat transfer unit.

In the configuration of this application example, the thermal conductivity of the belt on which the heat flow meter is mounted is lower than the thermal conductivity of the heat transfer unit. Therefore, for the heat flow generated in the thickness direction of the heat flow meter between the skin surface and the external environment, if is possible to reduce the heat leaking to the belt in a direction intersecting the thickness direction Of the heat flow meter from a contact portion with the heat flow meter. Accordingly, it is possible to suppress the error to be small in the measurement of the heat flow generated between the skin surface and the external environment.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described with reference to the drawings. The drawings to be used are illustrated appropriately to be scaled up or down or exaggerated so that portions to be described can be recognized. Further, constituent elements other than constituent elements necessary for description are omitted in some cases.

In the following embodiments, a mounting type biological information acquisition device which is mounted on an arm of a user and measures a heat discharge from a human body will be described as an example of an electronic device.

First Embodiment
Electronic Device

Figure 1:
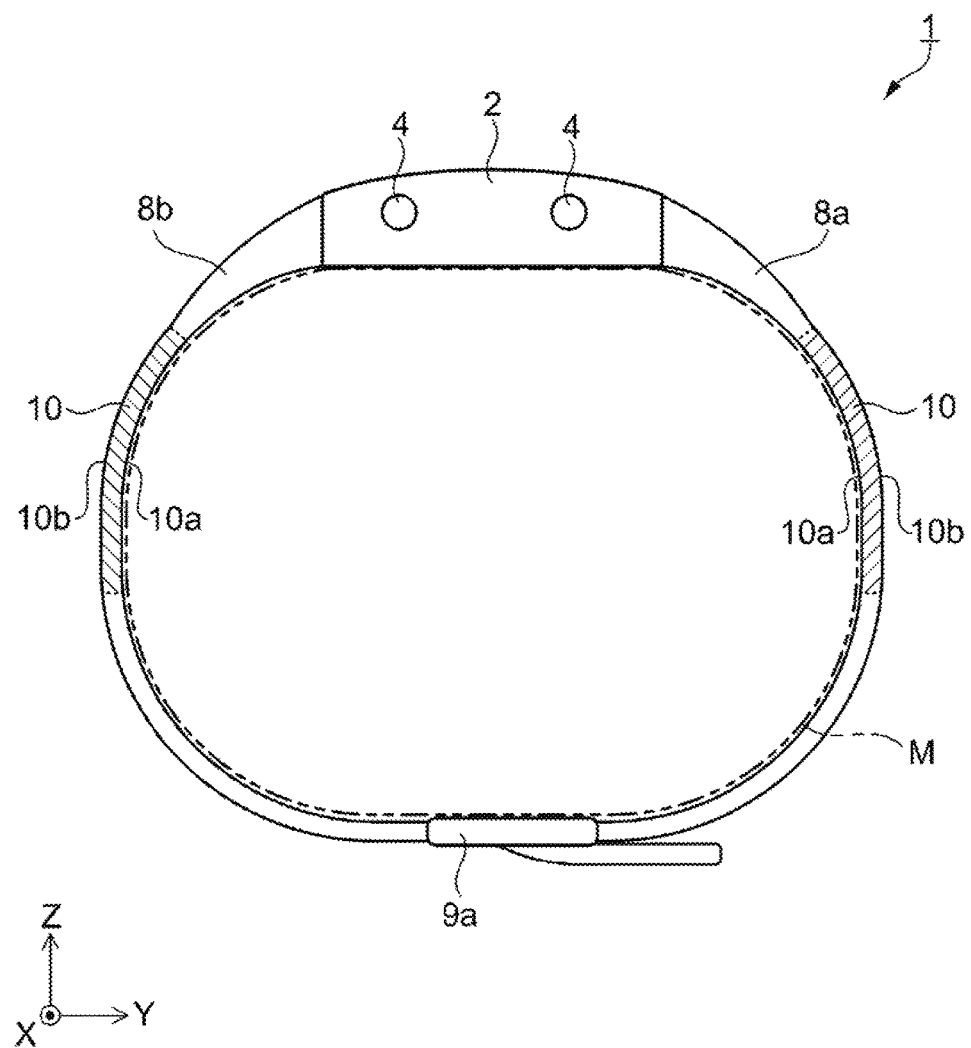
FIG. 1 is a side view illustrating a schematic configuration of an electronic device according to a first embodiment.
Figure 2A:
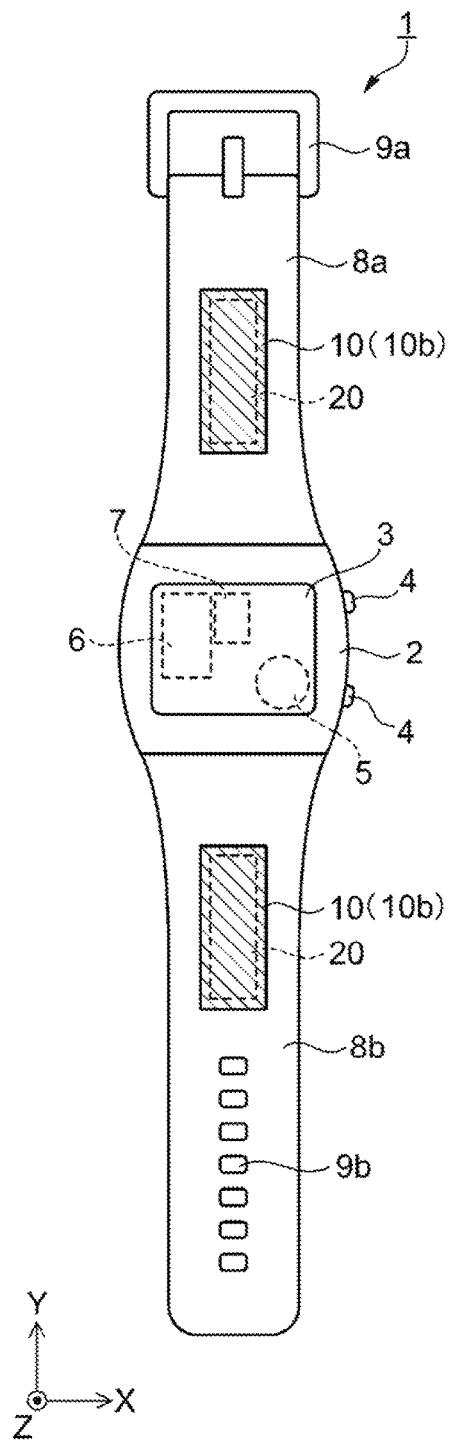
FIGS. 2A and 2B are plan views illustrating the configuration of the electronic device according to the first embodiment.
Figure 2B:
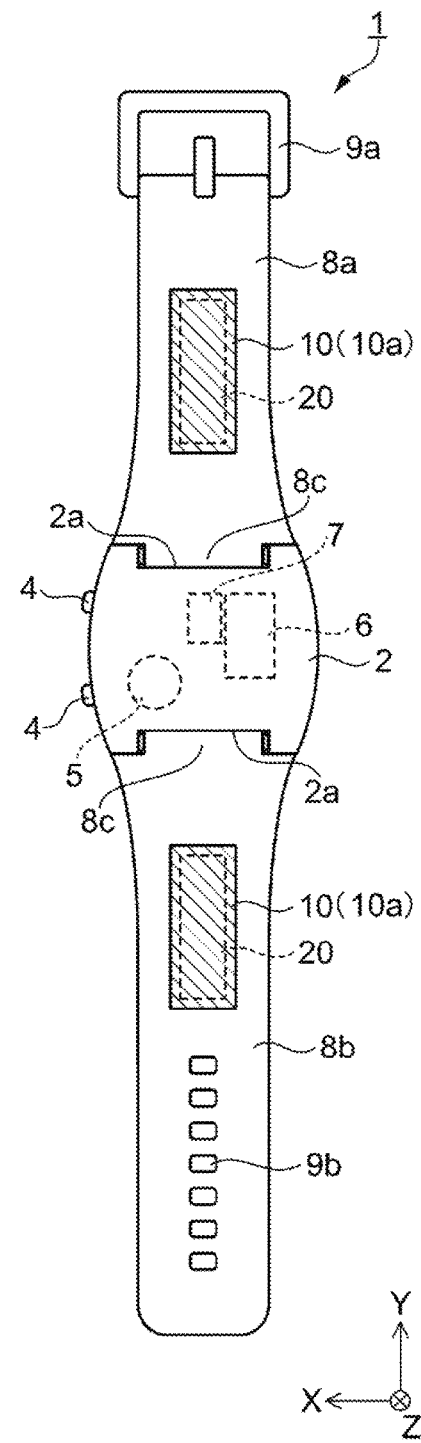
Figure 3:
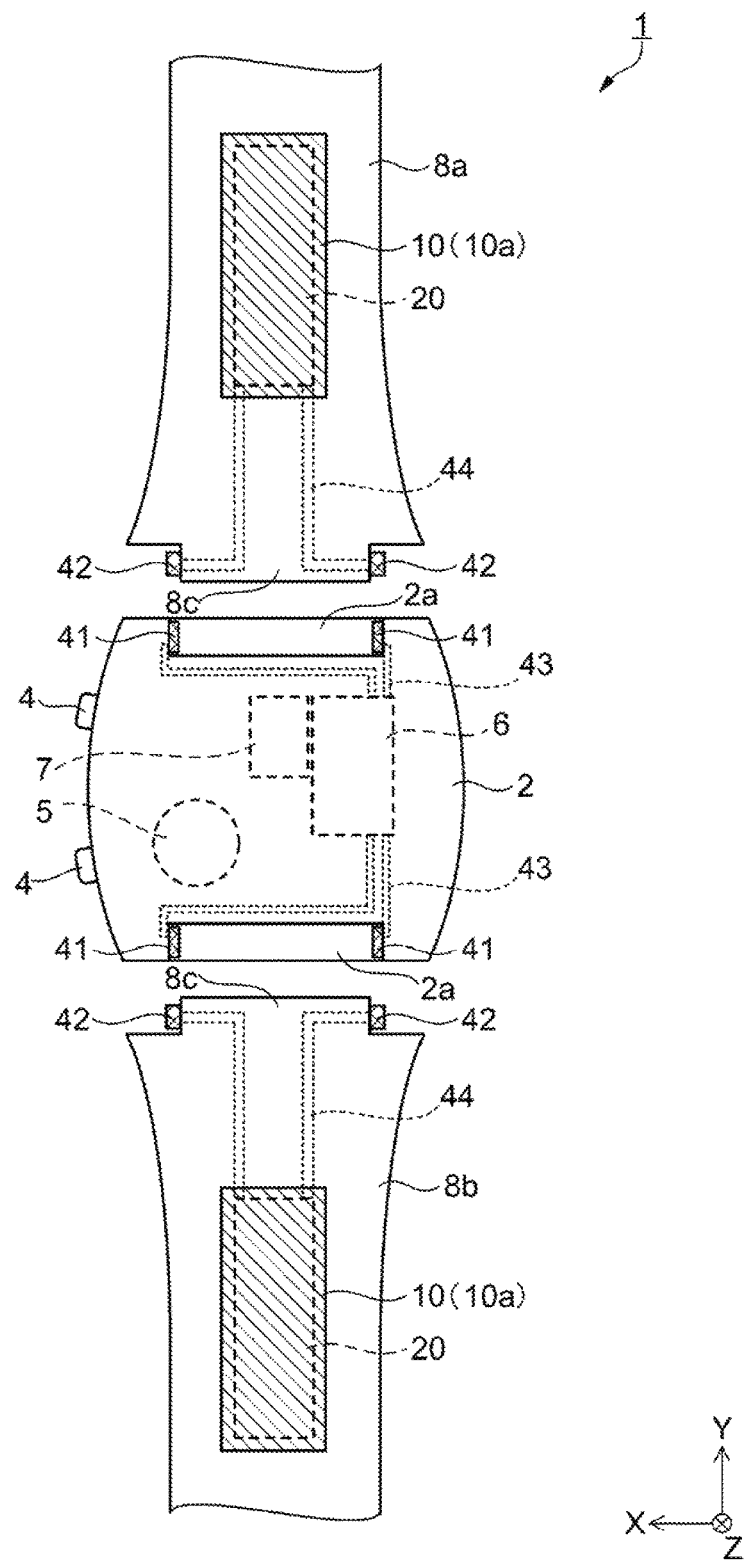
FIG. 3 is a plan view illustrating the configuration of the electronic device according to the first embodiment.
Figure 4:
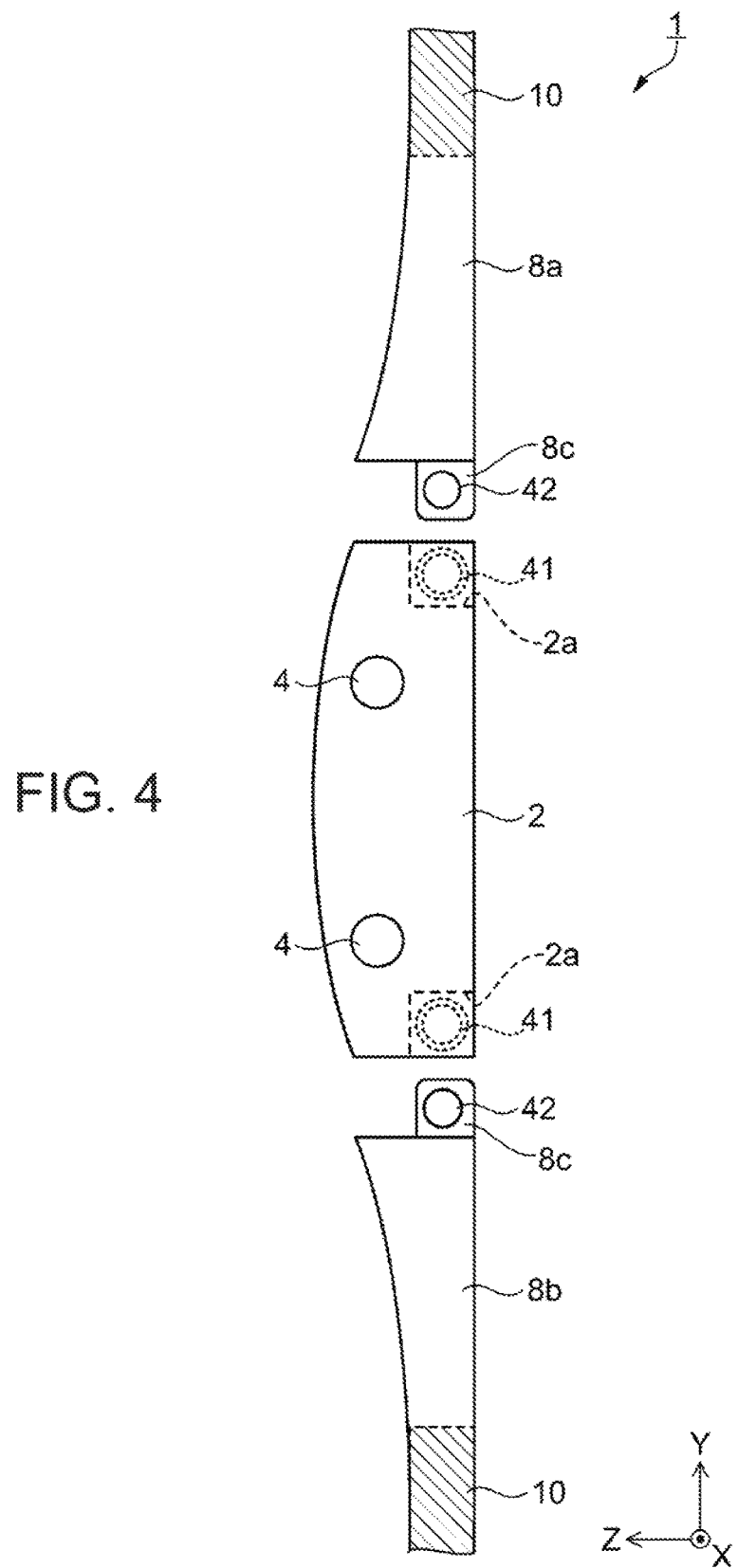
FIG. 4 is a side view illustrating the configuration of the electronic device according to the first embodiment.

First, a schematic configuration of an electronic device according to a first embodiment will be described with reference to FIGS. 1, 2A, 2B, 3, and 4. FIG. 1 is a side view illustrating a schematic configuration of the electronic device according to a first embodiment. FIGS. 2A, 2B, and 3 are plan views illustrating the configuration of the electronic device according to the first embodiment. FIG. 4 is a side view illustrating the configuration of the electronic device according to the first embodiment. In detail, FIG. 2A is a front view illustrating the electronic device and FIG. 2B is a rear view illustrating the electronic device. FIG. 3 is a rear view illustrating a state excluding belts 8a and 8b from a casing 2. FIG. 4 corresponds to a side view when the state of FIG. 3 is viewed from the lateral side.

FIG. 1 is a diagram schematically illustrating a state in which an electronic device 1 according to the first embodiment is mounted on an arm (human body) M of a user. As illustrated in FIG. 1, the electronic device 1 according to the first embodiment includes a casing 2 and one pair of belts 8a and 8b connected to the casing 2. A buckle 9a is fitted in the belt 8a and a plurality of holes 9b (see FIG. 2A) engaging with the buckle 3a are formed in the belt 8b.

In FIG. 1, the cross section of the arm M is schematically illustrated by a two-dot chain line. The electronic device 1 is a wristwatch type wearable device that is mounted by winding the casing 2 around the arm M of the user in a ring shape by the one pair of belts 8a and 8b and measures a heat discharge from a human body. In the embodiment, a side (inside) of the casing 2 and the belts 8a and 8b coming into contact with the surface of the arm M (hereinafter referred to as a skin surface) is referred to as a rear surface and an opposite side (outside) to the rear surface is referred to as a front surface. The electronic device 1 is mounted on the arm M of the user in a state in which the rear surface of the casing 2 and the rear surface of the belts 8a and 8b touch with the skin surface.

A normal, direction of the front surface of the casing 2 is referred to as a Z axis direction in which the upper side is positive in FIG. 1. A longitudinal direction of the arm M which is a direction intersecting the Z axis direction is referred to as an X axis direction in which the front side is positive in FIG. 1. A width direction of the arm M which is a direction intersecting the Z axis direction and the X axis direction, that is, an extension direction of the belts 8a and 8b, is referred to as a Y axis direction in which the side of the belt 8a is positive.

FIG. 2A is a plan view illustrating a state in which the electronic device 1 is detached from the arm M and is put on a flat surface so that the front surface side is oriented upward. FIG. 2B is a plan view illustrating a state in which the electronic device 1 is detached from the arm M and is put on the flat surface so that the rear surface side is oriented upward.

As illustrated in FIG. 2A, the casing 2 includes a display 3 on the front surface side. Although the details are not illustrated, the display 3 includes a display device and a touch panel integrated with the display device or stacked to be separated from the display device. Accordingly, the display 3 has a function of a display unit 35 (see FIG. 5) which displays information such as an image for the user and a function of an operation unit 34 (see FIG. 5) with which the user inputs various operations.

The casing 2 includes operation buttons 4 that function as an operation unit 34 on the lateral side (+X direction). The number of operation buttons 4, the shapes of the operation buttons 4, and disposition positions of the operation buttons 4 are not particularly limited. The user can perform various input operations such as a measurement start operation using the display 3 (touch panel), the operation button 4, or the like.

As illustrated in FIGS. 2A and 2B, a rechargeable battery 5, a control substrate 6, and a storage medium 7 are built in the casing 2. Besides, a communication device transmitting a measurement result of a heat flow to an external device, a reader/writer device reading and writing the measurement result of the heat flow on a memory card, or the like may be provided in the casing 2. As a charging scheme for the battery 5, for example, an electric contact may be separately provided on the rear surface side of the casing 2 and may be configured to be charged via a cradle via the electric contract, or a non-contact type cordless charging may be configured.

Although not illustrated, a central processing unit (CPU) or an integrated circuit (IC) are mounted on the control substrate 6. Besides, an application specific integrated circuit (ASIC) or necessary electronic components such as various integrated circuits can be mounted on the control substrate 6. A memory, a hard disk, or the like is used as the storage medium. The electronic device 1 realizes various functions such as heat flew measurement when the CPU mounted on the control substrate 6 executes a program stored in the storage medium 7.

The belts 8a and 8b extend in the Y axis direct ion. The belt 8a is connected to one end side (+Y direction side) of the casing 2 and the belt 8b is connected to the other side (−Y direction side) of the casing 2. The belts 8a and 8b are formed of a material with flexibility, such as a soft resin such as silicon or polyurethane, a leather, or a synthetic leather.

The buckle 9a is fitted to the end on the opposite side (+Y direction side) to the side of the belt 8a connected to the casing 2. The plurality of holes 9b engaging with the buckle 9a are formed on the opposite side (−Y direction side) to the side of the belt 8b connected to the casing 2. When one of the plurality of holes 9b engages with the buckle 9a, the belts 8a and 8b are connected to each other. By appropriately selecting the hole 9b engaging with the buckle 9a, the actual lengths of the belts 8a and 8b on the mounted state can be adjusted, and thus a tightening force of the belts 8a and 8b against the arm M can be accordingly adjusted.

A heat flow sensor 10 serving as a heat flow meter is provided in each of the belts 8a and 8b. The heat flow sensor 10 is embedded in each of the belts 8a and 8b. In other words, the heat flow sensors 10 are formed through the belts 8a and 8b in the Z axis direction and the side surfaces (the surface in the ±X direction and the surface in the ±Y direction) are joined to the belts 8a and 8b so that the front surface (the surface in the +Z direction) and the rear surface (the surface in the −Z direction) of the heat flow sensor 10 are exposed to the surface of each or the belts 8a and 8b. As a method of attaching the heat flow sensor 10 to each of the belts 8a and 8b, the side surface of the heat flow sensor 10 is adhered to each of the belts 8a and 8b by an adhesive or the heat flow sensor 10 maybe joined to each of the belts 8a and 8b by sewing.

The heat flow sensor 10 has flexibility and softness. The rear surface of the heat flow sensor 10 is referred to as a surface 10a (see FIG. 2B) and the front surface of the heat flow sensor 10 is referred to as a surface 10b (see FIG. 2A). When the electronic device 1 is mounted on the arm M of the user, the heat flow sensors 10 are bent along the curved surface of the arm M along with the belts 8a and 8b so that the surfaces 10a exposed to the ins ides of the belts 8a and 8b are disposed to come into contact with the surface of the arm M and the surfaces 10b exposed to the outside of the belts 8a and 8b come into contact with an external environment (see FIG. 1).

The heat flow sensor 10 includes a temperature difference measurement unit 20. As will be described in detail, the temperature difference measurement unit 20 has a function of measuring a temperature difference between the surface of a living body (in the embodiment, a skin surface of the user) and the external environment. The electronic device 1 measures a heat flow generated between the skin surface and the external environment based on a measurement result of the temperature difference measurement unit 20 included in the heat flow sensor 10 to measure a heat discharge from the human body.

As illustrated in FIGS. 3 and 4, concave portions 2a recessed from the rear surface side to the front surface side of the casing 2 are formed at both ends of the casing 2 in the Y axis direction. Connection portions 41 connecting the belts 8a and 8b are formed at both ends of the concave portions 2a in the X axis direction. The connection portions 41 are formed of a material such as a conductive metal. The connection portions 41 are electrically connected to the control substrate 6 by wirings 43 (see FIG. 3). Inside the casing 2, wirings are provided besides the wirings 43 illustrated in FIG. 3. The connection portion 41 has, for example, a hollow tubular shape.

The belts 8a and 8b each have a bulge portion 8c at the end on the side connected to the casing 2. When the bulge portions 8c of the belts 8a and 8b are inserted into the concave portions 2a of the casing 2, the belts 8a and 8b are connected to the casing 2 (see FIG. 2B). Connection portions 42 for connection to the casing 2 are formed at both ends of the bulge portion 8c in the X axis direction. The connection portions 42 are formed of a material such as conductive metal. The connection portions 42 are electrically connected to the temperature difference measurement unit 20 of the heat flow sensor 10 by wirings 44 (see FIG. 3). The connection portions 42 are formed in, for example, a bar shape and is configured to be expandable and contractable in the X axis direction by urging of a spring or the like.

The casing 2 and the belts 8a and 8b are mechanically connected and electrically connected by the connection portions 41 and 42. That is, the belts 8a and 8b are mechanically connected to the casing 2 by pushing the connection portions 42 of the belts 8a and 8b into the bulge portions 8c in the state illustrated in FIGS. 3 and 4 and inserting the bulge portions 8c into the concave portions 2a of the casing 2 so that the connection portions 42 are fit in the tubular connection portions 41.

By fitting the connection portions 42 in the connection portions 41, the connection portions 42 are electrically connected to the connection portions 41. Then, the temperature difference measurement units 20 of the heat flow sensors 10 provided in the belts 8a and 8b are electrically connected to the control substrate 6 built in the casing 2 via the connection portions 42 and 41.

The portions mechanically and electrically connecting the casing 2 to the belts 8a and 8b are not limited to the configuration realized through the connection portions 41 and 42 described above. For example, a configuration in which portions for mechanical connection and portions for electrical connection are different may be realized as in a configuration in which the belts 8a and 8b are fixed to the casing 2 by screws or the like and flexible substrates provided respectively are electrically connected.

Figure 5:
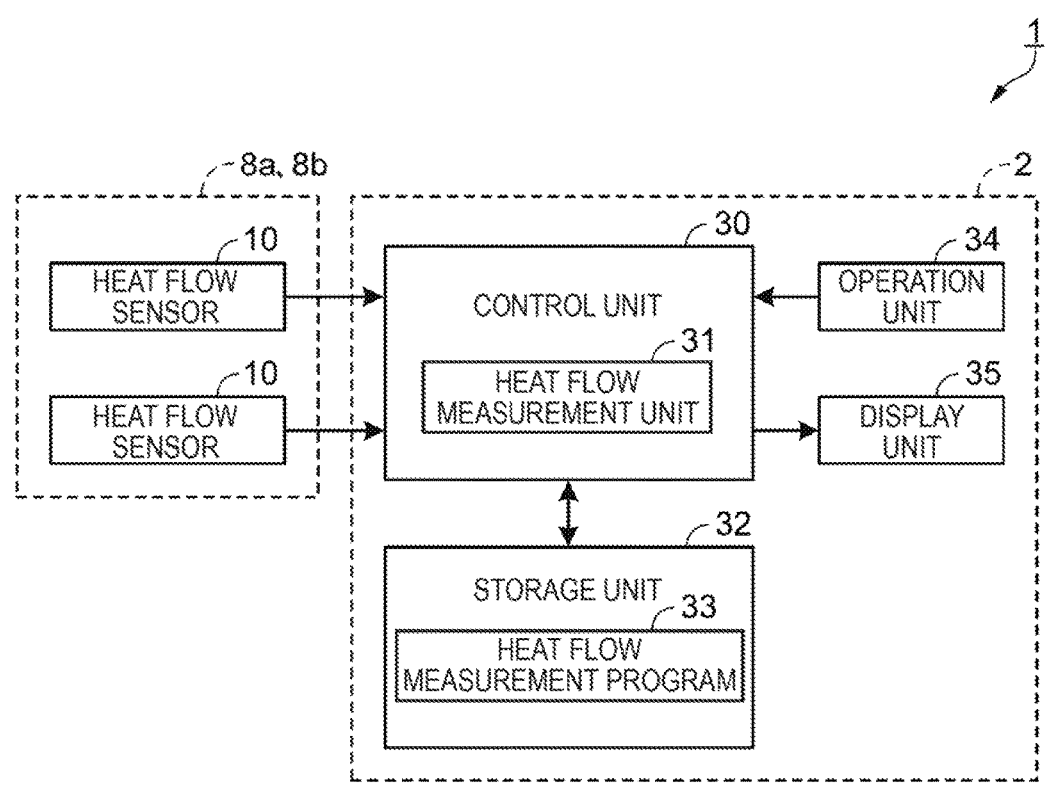
FIG. 5 is a block diagram illustrating a schematic functional configuration of the electronic device according to the first embodiment.

Next, a schematic functional configuration of the electronic device 1 according to the first embodiment will be described with reference to FIG. 5. FIG. 5 is a block diagram illustrating the schematic functional configuration of the electronic device according to the first embodiment. As illustrated in FIG. 5, the electronic device 1 includes two heat flow sensors 10 provided in the one pair of belts 8a and 8b and includes the operation unit 34, the display unit 35, a control unit 30, and a storage unit 32 provided in the casing 2.

The operation unit 34 is realized by an input device such as various switches such as a button switch, a lever switch, and a dial switch or a touch panel and outputs an operation signal according to an input operation to the control unit 30. In the embodiment, for example, the operation button 4 or the touch panel of the display 3 illustrated in FIG. 2A corresponds to the operation unit 34.

The display unit 35 is realized by a display device such as a liquid crystal display (LCD) or an organic electroluminescence (EL) display and displays various screens based on display signals input from the control unit 30. In the embodiment, for example, the display device of the display 3 illustrated in FIG. 2A corresponds to the display unit 35.

A measurement result of a heat flow or the like is displayed on the display unit 35. In the embodiment, for example, a measurement result of a heat flow is displayed in a current heat flow display screen or a heat flow change display screen graphing a heat flow change based on previous logging data according to a switching operation of a display mode on the operation unit 34.

The control unit 30 is a control device and an arithmetic device that generally controls each unit of the electronic device 1. The control unit 30 is realized by a microprocessor such as a central processing unit (CPU) or a graphic processing unit (GPU), an application specific integrated circuit (ASIC), a field-programmable gate array (FPGA), an integrated circuit (XC) memory, and the like. In the embodiment, for example, the CPU mounted on the control substrate 6 illustrated in FIG. 2A corresponds to the control unit 30. The control unit 30 includes a heat flow measurement unit 31 that measures a heat flow of a human body based on a measurement result of the heat flow sensor 10.

The storage unit 32 is realized by any of various IC memories such as a read-only memory (ROM), a flash RDM, and a random access memory (RAM) or a storage medium such as a hard dish. In the embodiment, for example, the storage medium 7 illustrated in FIG. 2A corresponds to the storage unit 32. The storage unit 32 stores programs operating the electronic device 1 and realizing various functions of the electronic device 1 or data used during execution of the programs in advance or temporarily at each processing time. The storage unit 32 stores a heat flow measurement program 33 that functions the control, unit 30 as the heat flow measurement unit 31 and executes a heat flow measurement process.

Measurement Principle of Heat Flow

Here, a measurement principle of a heat flow performed by the electronic device 1 will be described. In general, an object present in the atmosphere exchanges heat with surrounding substances or other objects. At this time the amount of heat per unit time emitted from a certain object or flowing in the object is referred to as a heat flow which is expressed using a unit such as [W (=J/s)] or [kcal/min].

A heat flow of an object is measured, for example, by providing heat flow sensors at a plurality of portions of a target object and measuring a temperature difference (temperature gradient) occurring between the heat flow sensors. This is based on the Fourier's law stating that a heat flow of transfer through an object is proportional to a temperature difference present in the object (Expression (1) below). In Expression (1), Q indicates a heat flow [W (J/s)], A indicates an area (m²) of an object, λ indicates thermal conductivity [W/(m×K)], d indicates the thickness [m] of the object, and ΔT indicates a temperature difference [K] present in the object.

$$Q = A \frac{\lambda}{d} \Delta T \tag{1}$$

Accordingly, when a human body is a target, the heat flow can be measured by providing a heat flow sensor on a skin surface and measuring a temperature difference occurring in the heat flow sensor through heat transfer between the skin surface and the external environment, for example, a temperature difference occurring in the heat flow sensor by deprival of heat from the surface (the side of the heat flow sensor coming into contact with the external environment) of the heat flow sensor due to the above-described heat transfer.

As described above, the electronic device 1 according to the embodiment is disposed so that the surface 10a exposed to the insides of the belts 8a and 8b comes into contact with the skin surface and the surface 10b exposed to the out sides of the belts 8a and 8b comes into contact with the external environment, by winding the belts 8a and 8b in which the heat flow sensors 10 are embedded around the arm M of the human body to be mounted (see FIG. 1). Then, the heat flow of the human body can be measured by measuring a temperature difference occurring between the surface 10a (the shin surface) and the surface 10b (the external environment) of the heat flow sensor 10.

Heat Flow Sensor

Figure 6:
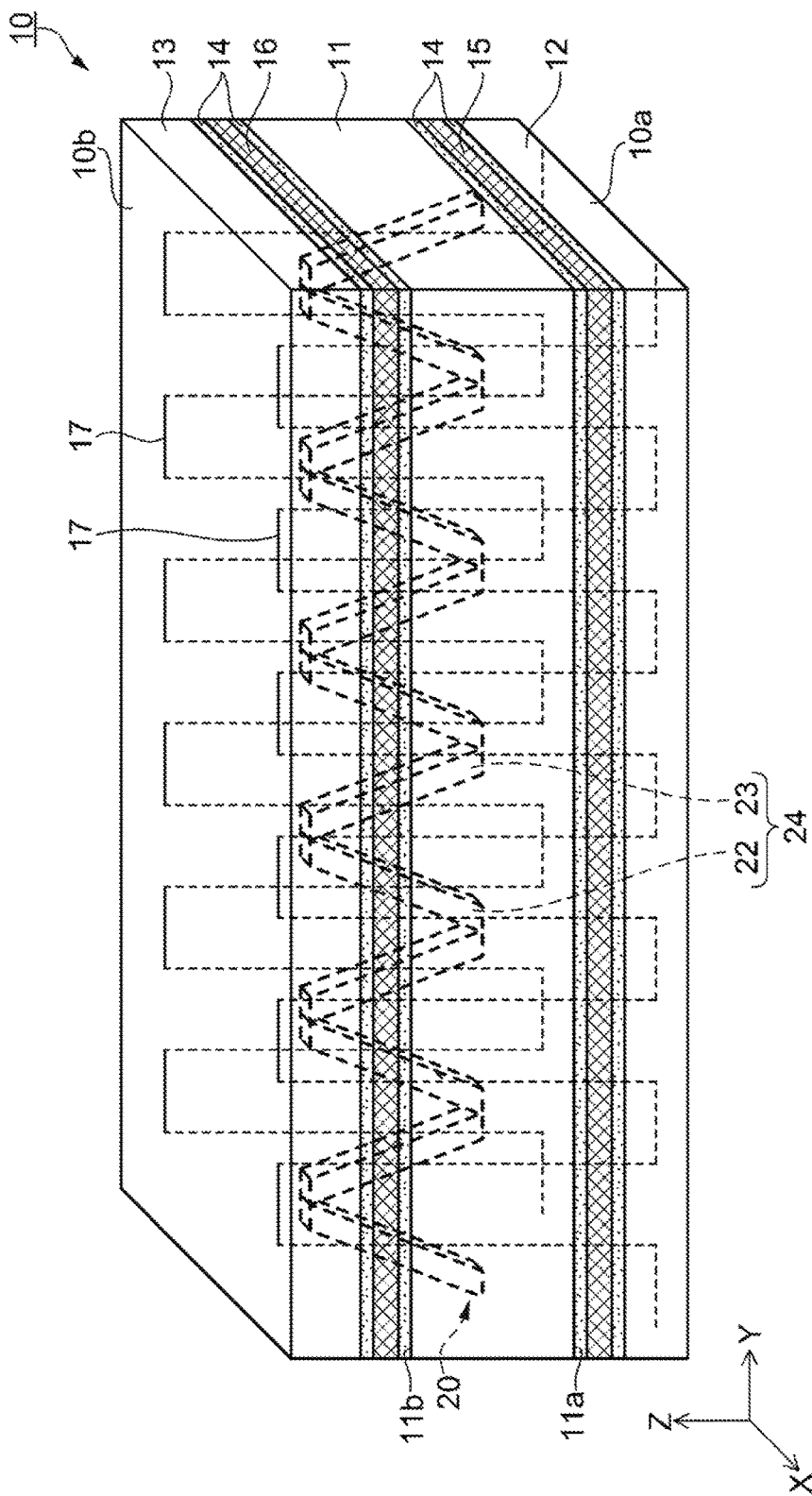
FIG. 6 is a perspective view schematically illustrating the configuration of a heat flow sensor according to the first embodiment.
Figure 7:
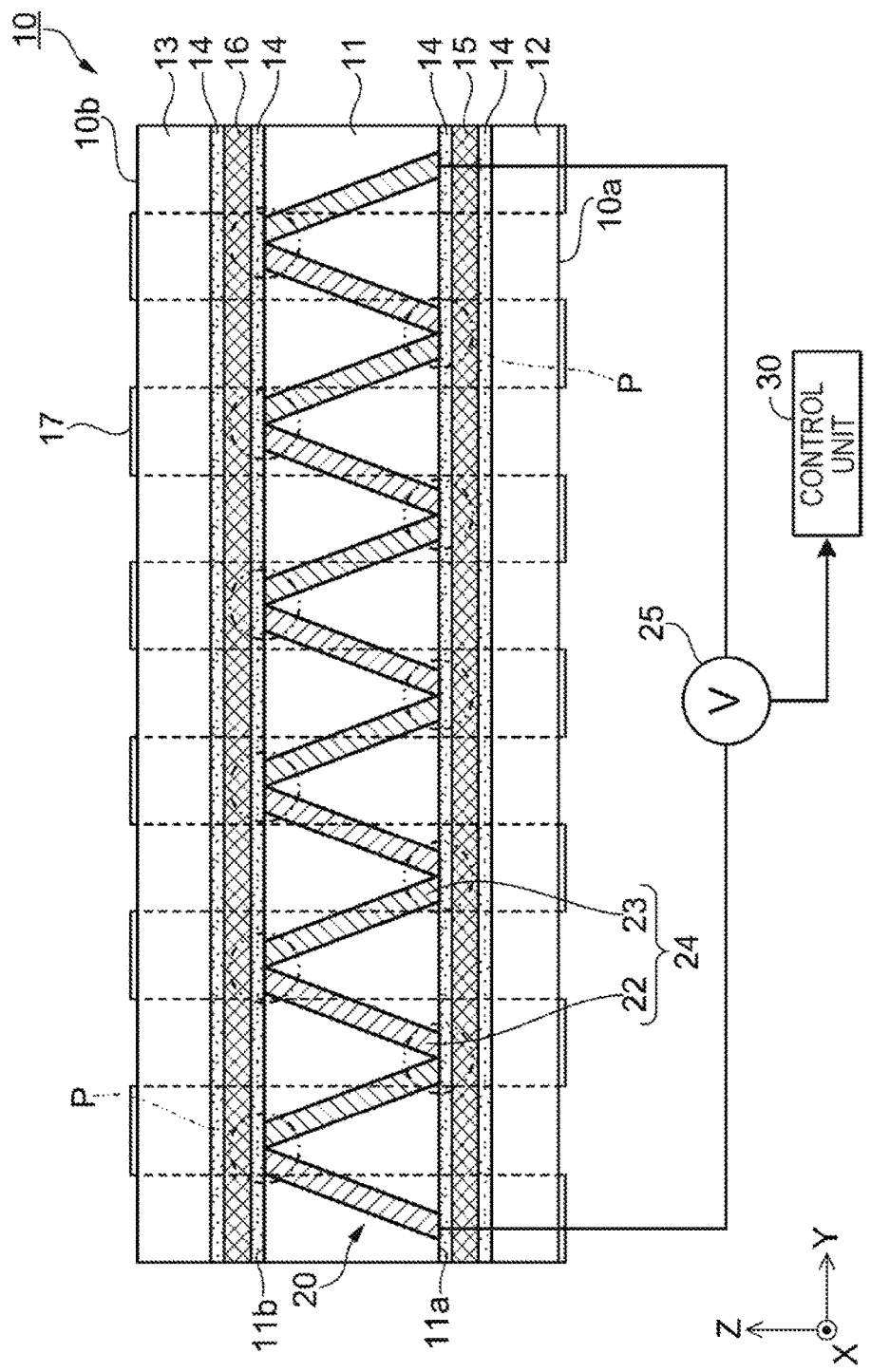
FIG. 7 is a sectional view schematically illustrating the configuration of the heat flow sensor according to the first embodiment.

Next, the configuration of the heat flow sensor according to the first embodiment will be described with reference to FIGS. 6 and 7. FIG. 6 is a perspective view schematically illustrating the configuration of the heat flow sensor according to the first embodiment. FIG. 7 is a sectional view schematically illustrating the configuration of the heat flow sensor according to the first embodiment. In FIGS. 6 and 7, the beat flow sensor 10 put on a flat surface by detaching the electronic device 1 from the arm M is illustrated, as in FIGS. 2A to 4.

As illustrated in FIGS. 6 and 7, the heat flow sensor 10 according to the first embodiment includes a first protective layer 12, a first heat diffusion layer 15, a heat transfer layer 11 serving as a heat transfer unit, a second heat diffusion layer 16, and a second protective layer 13 stacked in order in the +Z direction from the side of the surface 10a. The heat flow sensor 10 includes the temperature difference measurement unit 20 embedded in the heat transfer layer 11.

The heat transfer layer 11 has a flat plate shape. The surface of the heat transfer layer 11 on the rear surface side (−Z direction side) is referred to as a first surface 11a and the surface of the heat transfer layer 11 on the front surface side (+Z direction side) is referred to as a second surface 11b. The heat flow sensor 10 has a configuration in which the first heat diffusion layer 15 and the first protective layer 12 are disposed in order on the side of the first surface 11a of the heat transfer layer 11 and the second heat diffusion layer 16 and the second protective layer 13 are disposed in order on the side of the second surface 11b of the heat transfer layer 11.

Adhesive layers 14 are disposed to be adhered between the first protective layer 12 and the first heat diffusion layer 15, between the first beat diffusion layer 15 and the heat transfer layer 11, between the heat transfer layer 11 and the second heat diffusion layer 16, and between the second heat diffusion layer 16 and the second protective layer 13. The layers from the first protective layer 12 to the second protective layer 13 are sewn by sutures 17 so that the mutually adjacent layers are joined to each other.

The surface of the first protective layer 12 is the surface 10a of the heat flow sensor 10 and the surface of the second protective layer 13 is the surface 10b of the heat flow sensor 10. When the electronic device 1 is mounted on the arm M of the user, the heat flow sensor 10 is disposed so that the surface 10a comes into contact with the surface (the skin surface) of the arm M and the surface 10b is exposed to the external environment. Therefore, the first protective layer 12 comes into contact with the skin surface and the second protective layer 13 is exposed to the external environment.

Hereinafter, the configuration of each unit of the heat flow sensor 10 will be described. The heat transfer layer 11 is formed of a member having flexibility and good thermal conductivity. More specifically, the heat transfer layer 11 includes a first member having flexibility and a second member having higher heat conductivity than the first member. In the heat transfer layer 11, the second member is dispersed in the first member and a volume ratio of the second member is less than the volume ratio of the first member. Therefore, the heat transfer layer 11 has both of flexibility and thermal conductivity.

As the first member serving as a base material of the heat transfer layer 11, for example, a material having flexibility and softness, such as rubber such as natural rubber or synthetic rubber or a soft resin such as polyurethane or silicon can be used. As the second member dispersed in the base material of the heat transfer layer 11, for example, a thermally conductive filler such as a carbon black powder, a carbon fiber, a diamond powder, a silicon carbide powder, or a metal powder can be used.

To cause the heat transfer layer 11 to have the good flexibility and softness the Shore hardness of the heat transfer layer 11 (the first member) is preferably equal to or less than A50. The Shore hardness is measured by a type A durometer decided by JIS R 6253. To cause a temperature difference to occur for measurement of a heat flow between the first surface 11a and the second surface 11b of the heat transfer layer 11, the thickness of the heat transfer layer 11 (the first member) is preferably equal to or greater than 0.5 mm and equal to or less than 3 mm and is more preferably equal to or greater than 1.0 mm and equal to or less than 1.5 mm.

The thickness of the heat transfer layer 11 is preferably as thin as possible within a range in which a temperature difference occurs so that the heat flow can be measured. When the heat transfer layer 11 is thick, heat leaking in directions (the X axis direction and the Y axis direction) intersecting the heat, flow generated in the thickness direction (the Z axis direction) between the first surface 11a and the second surface 11b may increase, and thus there is a concern of an error occurring in the measurement of the heat flow.

To obtain good responsibility in the measurement of the heat flow, the thermal conductivity of the heat transfer layer 11 is preferably equal to or greater than 10 W/(m×K). The thermal conductivity of general rubber or resin is about 0.1 W/(m×K) to about 0.5 W/(m×K) and the thermal conductivity of the above-described thermally conductive filler is generally equal to or greater than 100 W/(m×K). By dispersing the second member (the thermally conductive filler) in the first member (base member) formed of rubber or a resin, it is possible to improve the thermal conductivity of the heat transfer layer 11 and improve responsibility when the heat flow is measured. For example, when the second member is dispersed at a ratio of 10% or more to the first member, the thermal conductivity of the heat transfer layer 11 can be set to be equal to or greater than 10 (m×K).

The first heat diffusion layer 15 and the second heat diffusion layer 16 are layers that cause a temperature distribution to be uniform in the planes of the first surface 11a and the second surface lib of the heat transfer layer 11. The thermal conductivity of each of the first heat diffusion layer 15 and the second heat diffusion layer 16 is preferably greater than 100 W/(m×K). By causing the temperature distribution in the planes of the first surface 11a and the second surface 11b of the heat transfer layer 11 to be more uniform with the first heat diffusion layer 15 and the second heat diffusion layer 16, the heat flow can be measured in a more stable state even when a variation occurs due to a contact state between the heat flow sensor 10 and the skin surface or a variation occurs due to the temperature distribution of the shin surface at the time of the measurement of the heat flow.

The Shore hardness of the first heat diffusion layer 15 and the second heat diffusion layer 16 is preferably equal to or less than A50 and the thicknesses of the first heat diffusion layer 15 and the second heat diffusion layer 16 are preferably about 0.1 mm to about 0.5 mm so that the flexibility and the softness of the heat transfer layer 11 are not damaged. As the materials of the first beat diffusion layer 15 and the second heat diffusion layer 16, for example, a carbon-based heat conduction sheet such as a graphite sheet or a carbon sheet or a metal thin film such as an aluminum sheet or a copper foil can be used.

The first protective layer 12 and the second protective layer 13 are layers that protect the heat transfer layer 11 or the first heat diffusion layer 15 and the second heat diffusion layer 16 from damage caused due to unexpected contact or the like with another object, As the material of the first protective layer 12 and the second protective layer 13, for example, a material formed of an organic matter such as silicon rubber and having Shore hardness of A50 or less so that the flexibility and the softness of the heat transfer layer 11, the first heat diffusion layer 15, and the second heat diffusion layer 16 are not damaged is preferably used. The material of the first protective layer 12 and the second protective layer 13 may be leather or synthetic leather. The thicknesses of the first protective layer 12 and the second protective layer 13 are preferably about 0.1 m to about 0.5 mm to protect the first heat diffusion layer 15 and the second heat diffusion layer 16 against damage.

As the adhesive layer 14, for example, a known adhesive capable of maintaining flexibility even after adhesion, such as a nitrile rubber adhesive or an acrylic adhesive, can be used. As the adhesive layer 14, a known adhesive in which a thermally conductive filler such as a metal powder or a carbon fiber is dispersed in such an adhesive may be used. The thickness of the adhesive layer 14 is preferably equal to or less than 0.1 mm. The thickness of the adhesive layer 14 is preferably as thin as possible within a range in which the adhesion force can be maintained without damage to the flexibility and the softness of the entire heat flow sensor 10.

The sutures 17 are used for suturing through the heat transfer layer 11, the first heat diffusion layer 15 and the first protective layer 12 adhered by the adhesive layer 14 on the side of the first surface 11a of the heat, transfer layer 11 to be stacked, and the second heat diffusion layer 16 and the second protective layer 13 adhered by the adhesive layer 14 on the side of the second surface 11b of the heat transfer layer 11 to be stacked. By performing the suturing by the sutures 17, the joining by the adhesive layers 14 between the layers is rarely peeled of ft As the sutures 17, for example, a synthetic fiber such as polyester or nylon or a natural fiber such as cotton or hemp can foe used.

By performing the suturing by the sutures 17, it is possible to mechanically reinforce the joining between the layers without damage to the flexibility and the softness of the entire heat flow sensor 10. The suturing positions of the suture 17 in the heat, flow sensor 10 are preferably outer frame portions of the heat flow sensor 10 to avoid the temperature difference measurement unit 20 embedded in the heat transfer layer 11 (see FIG. 6). When the reliably close contact and adhesion of the layers of the heat flow sensor 10 are ensured by the suturing by the sutures 17, the adhesive layers 14 may be omitted.

The temperature difference measurement unit 20 is a temperature difference output element buried in the heat transfer layer 11 and is configured by, for example, a thermopile. The temperature difference measurement unit 20 (thermopile) is configured by connecting a plurality of thermocouples 24 joining both ends of two different types of metal conductors 22 and 23 in series so that hot junctions and cold junctions are located on the first surface 11a (the skin surface side) and the second surface 11b (the external environment side) of the heat transfer layer 11. As the metal conductors 22 and 23, for example, alumel and chromel or copper and constantan can be used.

The heat of the skin surface is transferred to the first surface lie of the heat transfer layer 11 via the first heat diffusion layer 15 and the first protective layer 12, and the heat is emitted from the second surface 11b of the heat transfer layer 11 to the external environment via the second beat diffusion layer 16 and the second protective layer 13. The temperature difference measurement unit 20 outputs a temperature difference between the first surface 11a and the second surface 11b of the heat transfer layer 11, that is, between the hot junctions and the cold junctions, as a voltage signal. Accordingly, a voltage value detected by a voltmeter 25 is output as a measurement result of the temperature difference measurement unit 20 to the control unit 30 (see FIG. 7). In the control unit 30, the heat flow measurement unit 31 (see FIG. 5) performs a process of measuring the heat flow emitted from the human body (the skin surface) based on the measurement result of the temperature difference measurement unit 20.

The temperature difference measurement unit 20 according to the embodiment is configured as a thermopile in which the plurality of thermocouples 24 are connected in series. Therefore, the temperature difference measurement unit 20 measures the temperature difference based on temperature information at a plurality of points on the first surface 11a of the heat transfer layer 11 and temperature information at a plurality of points on the second surface 11b. In this way, since the temperature difference can be measured at the plurality of positions in the surface 10a at which the heat flow sensor 10 comes into contact with the skin surface, a more average value can be obtained than when the temperature difference is measured only at one position. By connecting the plurality of thermocouples 24 in series, a larger voltage signal can be output, compared to the case of only one thermocouple 24. Therefore, the heat flow can be measured more accurately.

Incidentally, to accurately measure heat (heat discharge) emitted from a human body, it is necessary to transfer the heat of the skin surface to the heat flow sensor without loss. The electronic device disclosed in JP-A-2011-120917 has a structure in which the attachment having flexibility and formed of metal with good thermal conductivity is brought into contact with a skin surface and the heat of the skin surface is transferred to the heat flow sensor via the attachment since the heat flow sensor has no flexibility. In such a structure, however, part of heat flows out to another member before the heat from the skin surface is transferred to the heat flow sensor. Therefore, an error occurs in the measurement of the heat flow and measurement accuracy of the heat discharge from the human body deteriorates.

Accordingly, to measure the heat flow without occurrence of an error, it is preferable to suppress the transfer loss of the heat by bringing the heat flow sensor into direct contact with the skin surface. However, since the heat flow sensor is formed of a bald material as a base material, the heat flow sensor has no flexibility. Further, when the heat flow sensor with no flexibility is brought into contact with an object having a curved surface, such as a human body (the arm M), an air layer easily occurs between the heat flow sensor and the skin surface.

Here, the heat flow sensor generally outputs the heat flow (temperature difference) detected on the entire surface coming into contact with an object (skin surface) as one voltage signal. As expressed in Expression (1) described above, the heat flow Q is proportional to the area A of an object. Therefore, when the contact area between the heat flow sensor and the object decreases, the heat flow measured by the heat flow sensor also decreases.

Therefore, when an air layer occurs in a part between the heat flow sensor and the skin surface, the actual contact area between the heat flow sensor and the skin surface decreases to the extent of the occurrence of the air layer and the heat transferred to the heat flow sensor decreases. Therefore, the heat flow measured by the heat flow sensor is less than the actually generated heat flow. When the wearer performs a motion of moving his or her arm or an exercise and thus the contact area between the heat flow sensor and the skin surface varies due to the occurrence of the air layer, the heat flow measured by the heat flow sensor also varies. As a result, in the heat flow sensor with no flexibility, an error occurs in the measurement of the heat flow and the measurement accuracy of the heat discharge from the human body deteriorates.

In the electronic device 1 according to the embodiment, the heat flow sensor 10 comes into direct contact with the skin surface. The heat flow sensor 10 has the flexibility and the softness. Therefore, when the electronic device 1 is mounted on an object having a curved surface such as a human body, the heat flow sensor 10 is bent along the surf ace of the arm M to be fitted on the skin surface. Therefore, since close contact with the skin surface is improved and the air layer rarely occurs between the heat flow sensor 10 and the skin surface, a decrease in the contact area is suppressed and the variation in the contact area is also suppressed. As a result, since the error can be decreased in the measurement of the heat flow generated between the skin surface and the external environment, the heat flow of the human body can be measured with high accuracy.

To measure the heat flow of the human body with high accuracy in the heat flow sensor 10, the belts 8a and 8b in which the heat flow sensor 10 is embedded are preferably formed of a material with lower thermal conductivity than the heat flow sensor 10 (the heat transfer layer 11). This is because the heat transferred in the thickness direction of the heat flow sensor 10 flows out in the direction intersecting the thickness direction of the heat flow sensor 10 from the contact portion with the heat flow sensor 10 to the belts 8a and 8b, and thus the error occurring in the measurement of the heat flow is suppressed. The thermal conductivity of the belts 8a and 8b is preferably less than 1 W/(m×K).

The belts 8a and 8b are preferably formed of a material with flexibility equal to or greater than the heat flow sensor 10. This is because the heat flow sensor 10 is well brought into contact with an object having a curved surface, such as the human body (the arm M), when the electronic device 1 is mounted on the human body (the arm M) with the belts 8a and 8b. The Shore hardness of the belts 8a and 8b is preferably equal to or less than A50.

Second Embodiment

In a second embodiment, the overall configuration of the electronic device 1 is the same as the configuration in the first embodiment, but the configuration of the temperature difference measurement unit in the heat flow sensor is different. Here, differences from the first embodiment will be described in the configuration of a heat flow sensor (temperature difference measurement unit) according to the second embodiment.

Heat Flow Sensor

Figure 8:
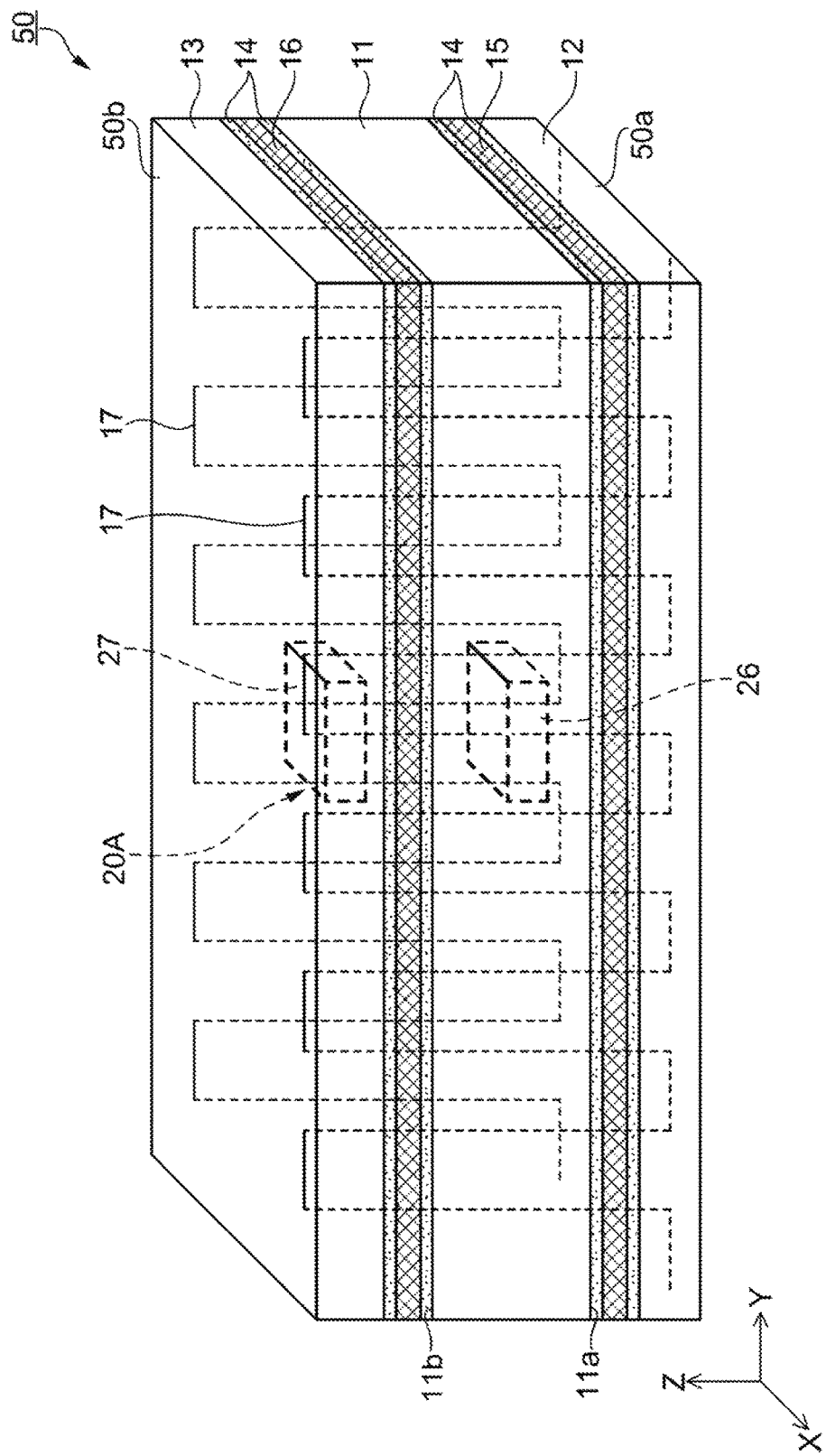
FIG. 8 is a perspective view schematically illustrating the configuration of a heat flow sensor according to a second embodiment.
Figure 9:
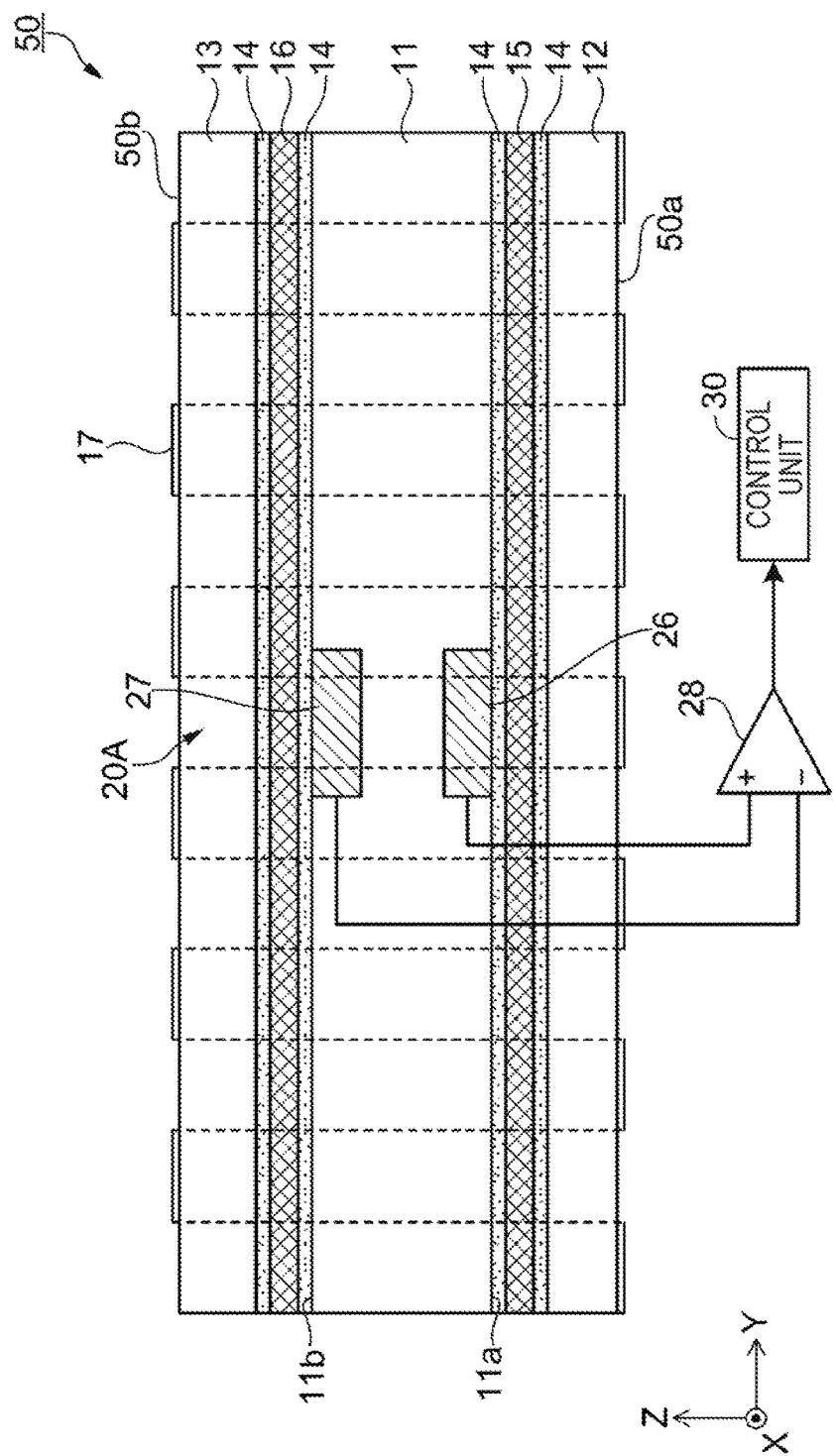
FIG. 9 is a sectional view schematically illustrating the configuration of the heat flow sensor according to the second embodiment.

The heat flow sensor according to the second embodiment will be described with reference to FIGS. 8 and 9. FIG. 8 is a perspective view schematically illustrating the configuration of the heat flow sensor according to the second embodiment. FIG. 9 is a sectional view schematically illustrating the configuration of the heat flow sensor according to the second embodiment. The same reference numerals are given to the same constituent elements as those of the first embodiment and the description thereof will be omitted.

As illustrated in FIGS. 8 and 9, a heat flow sensor 50 according to the second embodiment includes a surface 50a that comes into contact with a skin surface and a surface 50b that comes into contact with an external environment. The heat flow sensor 50 includes a first protective layer 12, a first heat diffusion layer 15, a heat transfer layer 11, a second heat diffusion layer 16, and a second protective layer 13 stacked in order in the +Z direction from the surface 50a. The heat flow sensor 50 includes a temperature difference measurement unit 20A embedded in the heat transfer layer 11.

The temperature difference measurement unit 20A includes a temperature element 26 disposed on the first surface 11a (skin surface side) of the heat transfer layer 11, a temperature element 27 disposed at a position facing the temperature element 26 on the second surface 11b (external environment side) of the heat transfer layer 11, and a differential amplifier 28 (see FIG. 9) performing differential amplification on an output temperature of the temperature element 26 and an output temperature of the temperature element 27. The temperature difference measurement unit 20A outputs a temperature difference between the first surface 11a and the second surface 11b of the heat transfer layer 11 as a measurement result to the control unit 30 (see FIG. 9). Thermistors, thermocouples, or the like can be used in the temperature elements 26 and 27.

In the control unit 30, the heat flow measurement unit 31 (see FIG. 5) performs a process of measuring a heat flow of a human body using the measurement result from the temperature difference measurement unit 20A according to Expression (2) below. In Expression (2), Q indicates a heat flow [W (J/s)], A indicates an area [m$^2$] of an object, λ indicates thermal conductivity [W/(m×K)] and d indicates the thickness [m] of the object. Ta indicates an output temperature [K] of the temperature element 26 and Tb indicates an output temperature [K] of the temperature element 27.

$$Q = A\frac{\lambda}{d}(T_a - T_b) \qquad (2)$$

When the heat flow sensors 50 according to the second embodiment is embedded in the belts 8a and 8b to be used in the electronic device 1, the heat flow sensors 50 having flexibility and softness come into direct contact with the skin surface, as in the first embodiment. Accordingly, since the heat flow generated between the skin surface and the external environment can be measured with high accuracy, the heat flow of the human body can be measured with high accuracy.

When the heat flow sensor 10 (the temperature difference measurement unit 20) according to the first embodiment is compared to the heat flow sensor 50 (the temperature difference measurement unit 20A) according to the second embodiment, the heat flow sensor 10 (the temperature difference measurement unit 20) using the thermopile can be thinned and processing is easy. Since the heat flow sensor 10 (the temperature difference measurement unit 20) can measure a temperature difference at a plurality of positions and outputs a large output signal (voltage signal), the heat flow can be measured more accurately.

The above-described embodiment is merely one kind of the invention and can be modified and applied in any form within the scope of the invention. As modification examples, for example, the followings can be considered.

MODIFICATION EXAMPLE 1

In the foregoing embodiment, the heat flow sensors 10 and 50 are configured to be embedded in parts of the belts 8a and 8b in the extension directions of the belts 8a and 8b. However, the heat flow sensors 10 and 50 may be configured to be embedded in the entire belts 8a and 8b in the extension directions of the belts 8a and 8b. In such a configuration, the contact areas of the heat flow sensors 10 and 50 with the circumferential surface of the arm M increase. Therefore, it is possible to further improve the measurement accuracy of the heat flow of the human body.

MODIFICATION EXAMPLE 2

In the foregoing embodiment, to mount the electronic device 1 on the arm M of the human body, the belts 8a and 8b in which the buckle 9a engages with the hole 9b are used. However, a surface fastener or the like may be used instead of the buckle 9a. Alternatively, a belt, a magic tape (registered trademark), or the like fixed by a buckle without using a hole may be used instead of the belts 8a and 8b.

MODIFICATION EXAMPLE 3

In the foregoing embodiment, the electronic device 1 is mounted on the arm M of the human body, but a part on which the electronic device 1 is mounted is not limited to the arm M. For example, the electronic device may be mounted on a part such as an upper arm, a belly, a thigh, a calf, an ankle, a neck, or a head. In this case, the belts 8a and 8b may be lengthened or parts of the belts 8a and 8b may be formed of an elastic material. The belts 8a and 8b on which the heat flow sensors 10 and 50 are embedded, may be detached from the electronic device 1 to be usable. Alternatively, the heat flow sensors 10 and 50 with a length or width proper for a measurement portion may be prepared separately. A measurement target is not limited to a human body, but may be, for example, the body of an animal, a trunk or a branch of a plant, or an artificial object such as an electric pole or a pillar.

MODIFICATION EXAMPLE 4

In the foregoing embodiment, the heat flow meter measuring a heat flow of a human body has been exemplified as the electronic device 1, but the invention is not limited to this form. For example, the invention may also be applied to a calorimeter, a consumption calorie meter, a metabolic meter, a metabolic function measurement device, or an automatic nerve function measurement device. Further, the invention may also be applied to a sports device measuring a calorific value of a muscle, a watching device targeting a mountain climber, an aged person, or a child, or a toy reflecting a measurement result of biological information to an event of a virtual space.

What is claimed is:
1. A heat flow meter comprising:
a heat transfer unit that has first and second surfaces confronting each other and has flexibility; and
a temperature difference measurement unit that is embedded in the heat transfer unit and that measures a temperature difference between the first and second surfaces of the heat transfer unit, wherein the heat transfer unit further includes a first member having flexibility and a second member dispersed in the first member, the second member having higher thermal conductivity than the first member.

2. The heat flow meter according to claim 1, wherein a thickness of the heat transfer unit is equal to or greater than 0.5 mm, thermal conductivity of the heat transfer unit is equal to or greater than 10 W/(mxK), and Shore hardness of the heat transfer unit is equal to or less than A50.

3. The heat flow meter according to claim 2, wherein a heat diffusion layer with thermal conductivity greater than 100 W/(mxK) is disposed on the first surface.

4. The heat flow meter according to claim 3, wherein a protective layer formed of an organic substance is disposed on a surface of the heat diffusion layer.

5. The heat flow meter according to claim 4, wherein the Shore hardness of the protective layer is equal to or less than A50.

6. The heat flow meter according to claim 4, wherein the heat transfer unit, the heat diffusion layer, and the protective layer are joined to each other by sewing.

7. The electronic device according to claim 3, wherein the heat diffusion layer causes a temperature distribution to be uniform in the plane of the first surface.

8. The heat flow meter according to claim 1, wherein the temperature difference measurement unit measures a temperature difference based on temperature information at a plurality of points of the first surface and temperature information at a plurality of points of the second surface.

9. An electronic device comprising:

a belt on which a heat flow meter including a heat transfer unit that has first and second surfaces confronting each other and has flexibility and a temperature difference measurement unit that measures a temperature difference between the first and second surfaces of the heat transfer unit is mounted;

a casing that is connected to the belt; and a control unit that is provided inside the casing and that controls the heat flow meter, wherein the heat transfer unit further includes a first member having flexibility and a second member dispersed in the first member, the second member having higher thermal conductivity than the first member.

10. The electronic device according to claim 9, wherein thermal conductivity of the belt is less than thermal conductivity of the heat transfer unit.

* * * * *